US009888896B2

(12) United States Patent
Lauritsch et al.

(10) Patent No.: US 9,888,896 B2
(45) Date of Patent: Feb. 13, 2018

(54) DETERMINING A THREE-DIMENSIONAL MODEL DATASET OF A BLOOD VESSEL SYSTEM WITH AT LEAST ONE VESSEL SEGMENT

(71) Applicants: Günter Lauritsch, Nürnberg (DE);
Thomas Redel, Poxdorf (DE);
Christopher Rohkohl, Hattingen (DE);
Michael Scheuering, Nürnberg (DE)

(72) Inventors: Günter Lauritsch, Nürnberg (DE);
Thomas Redel, Poxdorf (DE);
Christopher Rohkohl, Hattingen (DE);
Michael Scheuering, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 211 days.

(21) Appl. No.: 14/789,413

(22) Filed: Jul. 1, 2015

(65) Prior Publication Data

US 2016/0012636 A1 Jan. 14, 2016

(30) Foreign Application Priority Data

Jul. 10, 2014 (DE) .................. 10 2014 213 408

(51) Int. Cl.
*G06T 11/60* (2006.01)
*A61B 6/00* (2006.01)
(Continued)

(52) U.S. Cl.
CPC .............. *A61B 6/504* (2013.01); *A61B 6/032* (2013.01); *A61B 6/5205* (2013.01);
(Continued)

(58) Field of Classification Search
None
See application file for complete search history.

(56) References Cited

U.S. PATENT DOCUMENTS 6,047,080 A 4/2000 Chen et al.
8,638,999 B2 1/2014 Xu et al.
(Continued)

FOREIGN PATENT DOCUMENTS

DE 102007003260 A1 10/2007

OTHER PUBLICATIONS

Expectation maximization strategies for multi-atlas multi-label segmentation; Rohlfing et al., Information Processing in Medical Imaging Proceedings of the Conference, 2003, pp. 210-221, vol. 18.
(Continued)

*Primary Examiner* — Ryan M Gray
(74) *Attorney, Agent, or Firm* — Lempia Summerfield Katz LLC

(57) ABSTRACT

A three-dimensional model dataset of a blood vessel system of a patient including at least one the vessel system is determined from a number of projection images, which have been recorded from different recording angles, of the blood vessel system The projection images are divided up into image areas each containing at least one pixel. A feature vector is determined for each of the image areas. Classification information, which describes how the respective image area belongs or does not belong to a vessel segment of the blood vessel system defined in accordance with anatomical specification data, is defined for each of the image areas by applying a classification function to the feature vector assigned to the image area. The classification function has been trained by training data records annotated with classification information obtained from at least one person other than the patient. The blood vessel system in the projection images is segmented by grouping image areas with the same classification information. The three-dimensional model dataset is calculated as a function of the
(Continued)

segmented projection images and the classification information.

21 Claims, 2 Drawing Sheets

(51) Int. Cl.
G06T 17/00 (2006.01)
A61B 6/03 (2006.01)
(52) U.S. Cl.
CPC .......... *A61B 6/5288* (2013.01); *A61B 6/5294* (2013.01); *G06T 11/60* (2013.01); *G06T 17/00* (2013.01); *A61B 6/4441* (2013.01); *G06T 2200/04* (2013.01); *G06T 2210/41* (2013.01)

(56) References Cited

U.S. PATENT DOCUMENTS

| | | | |
|---|---|---|---|
| 2007/0237373 A1 | 10/2007 | Kiraly et al. | |
| 2011/0298793 A1* | 12/2011 | Lauritsch | A61B 6/504 345/419 |
| 2012/0213423 A1* | 8/2012 | Xu | A61B 5/0073 382/131 |
| 2013/0216110 A1* | 8/2013 | Zheng | G06T 7/66 382/128 |
| 2013/0315458 A1* | 11/2013 | Beymer | G06T 7/0085 382/130 |
| 2014/0254900 A1* | 9/2014 | Sturm | A61B 5/0037 382/128 |
| 2015/0282765 A1* | 10/2015 | Goshen | A61B 6/032 600/408 |

OTHER PUBLICATIONS

German National Refusal for related German Application No. 10 2014 213 408.0 dated Oct. 21, 2015, with English Translation.
Probabilistic Boosting Trees for Automatic Bone Removal from CT Angiography Images, Arne Militzer and Fernando Vega-Higuera; Arne Militzer and Fernando Vega-Higuera, "Probabilistic Boosting Trees for Automatic Bone Removal from CT Angiography Images", Proc of SPIE, vol. 7259, doi: 10.1117/12.811886, Oneline Publication Date: Mar. 27, 2009.
Artis one—Floor-mounted system for uncompromised imaging, Data Sheet, Siemens AG, Healthcare Sector, Erlangen, Order No. A91AX-81300-11T1-7600, pp. 1-32, Oct. 2013.
Frangi et. al.:"Multiscale Vessel Enhancement Filtering," vol. 1496/ 1998, 130, MICCAI 1998.
German Office Action for related German Application No. 10 2014 213 408.0, dated Feb. 9, 2015, with English Translation.
Mingqing Chen et al.: "Automatic Extraction of 3D Dynamic Left Ventricle Model from 2D Rotational Angiocardiogram", MICCAI 2011, Part III, Lecture Notes in Computer Science vol. 6893, pp. 471-478, 2011.
Smets C. et al., "An expert system for the labeling and 3D reconstruction of the coronary arteries from two projections," The International Journal of Cardiac Imaging; 5.2-3, pp. 145-154, 1990.
Syngo Workplace—Angio/Quant, Operator Manual, Siemens AG, Medical Solutions, Angiography & Interventional X-Ray Systems, Siemensstr. 1, 91301 Forchheim, www.siemens.com/healthcare, Order No. AX42-010.621.71.01.02, pp. 143-189, Apr. 2011.
Vikas Singh et al.: "A Linear Programming Based Algorithm for Determining Corresponding Point Tuples in Multiple Vascular Images", Proc. of SPIE,vol. 6144, 61442D-1, pp. 1-12, 2006.
Yefeng Zheng, et al., "Marginal Space Learning for Efficient Detection of 2D/3D Anatomical Structures in Medical Images", In Information Processing in Medical Imaging, pp. 411-422, Jul. 5, 2009.
Zheng Yefeng et al.: "Four-Chamber Heart Modeling and Automatic Segmentation for 3-D Cardiac CT Volumes Using Marginal Space Learning and Steerable Features", IEEE Transaction on Medical Imaging, vol. 27, No. 11, pp. 1668-1681, Nov. 2008.

* cited by examiner

DETERMINING A THREE-DIMENSIONAL MODEL DATASET OF A BLOOD VESSEL SYSTEM WITH AT LEAST ONE VESSEL SEGMENT

RELATED CASE

This application claims the benefit of DE 102014213408.0, filed on Jul. 10, 2014, which is hereby incorporated by reference in its entirety.

FIELD

The embodiments relate to a method for determining a three-dimensional model dataset of a blood vessel system including at least one vessel segment of a patient.

BACKGROUND

It is advantageous, particularly for planning and monitoring of catheter interventions, to use a three-dimensional model of a blood vessel system of a patient. Such a three-dimensional presentation is mostly intended to be reconstructed from a number of two-dimensional image recordings, especially x-ray recordings. In principle, it would be possible in such cases to calculate a 3D presentation from a number of two-dimensional projection images of vessels, especially with administration of contrast media. In everyday clinical practice, however, additional requirements are to be placed on the imaging of the blood vessel system. Thus, images are typically to be recorded within a small area of rotation of a C-arm system in order not to disturb the clinical workflow. For dose reduction, the number of projection images recorded is typically restricted as far as possible. Recording images of the blood vessel system is also made more difficult by the fact that vessels in the heart region move a great deal. By selecting projection images from a specific heart phase, a process known as EKG gating, the movement may be practically frozen. There are still smaller variances in the 3D position. In addition, the number of projection images available for a reconstruction is reduced by such EKG gating.

Tomographic image reconstruction is typically not possible under these conditions. As an alternative, symbolic 3D reconstructions are used. To create this type of symbolic 3D reconstruction, first of all, suitable 2D projection images are selected manually by a user, and individual vessels are segmented manually in the selected projection images. After a rough specification of an estimated vessel center line by a user, an exact center line is determined by a computing device. Thereafter, with the aid of the segmentation, the associated vessel edges are found and the vessel radii for this center line are computed.

To determine a 3D center line and a 3D vessel diameter for an individual vessel segment (e.g., a segment of the vessel between two branches or bifurcations in the vessel system) landmarks are detected automatically in the projection images. The landmarks are registered between different projection images, and information about the respective recording geometries of the projection images is additionally used.

The manual segmentation of projection images, as well as the specification of an approximate vessel center line for a relevant vessel are relatively complex. In addition, tight restrictions are imposed on the automatic detection of landmarks in the methods described, so that only individual, short vessel segments may be reconstructed.

SUMMARY AND DESCRIPTION

The scope of the present invention is defined solely by the appended claims and is not affected to any degree by the statements within this summary.

The underlying object of one or more of the present embodiments is thus to specify a method for determining a three-dimensional model dataset of the vessel system, where the method makes an automated segmentation of the vessel system possible and with which especially 3D model datasets of the blood vessel system may be created including a number of vessel segments.

The object is achieved by a method of the type stated above, including: dividing the projection images up into image areas each containing at least one pixel; determining a feature vector which includes at least image data of at least the image area assigned to the feature vector and/or computation data computed as a function of this image data, for each of the image areas; defining classification information that describes how the respective image area belongs to a vessel segment of the blood vessel system defined in accordance with anatomical specification data, especially in accordance with an anatomical atlas, or describes how the respective image area does not belong to the blood vessel system, for each of the image areas by applying a classification function to the feature vector assigned to the image area, wherein the classification function has been trained by training data records annotated with classification information obtained from at least one person other than the patient; segmenting the blood vessel system in the projection images by grouping of image areas with the same classification information; and computing the three-dimensional model dataset as a function of the segmented projection images and the classification information.

In accordance with one embodiment, it is proposed to perform a segmentation of the projection images by using a learning-based classification function. There is also provision for the classification function to be trained by machine learning, in order to allocate classification information to individual image areas. Which of a number of predetermined image segments are classified as showing a specific image area or whether a vessel segment is shown at all. Unlike conventional approaches to automatic segmentation of image recordings, the segmentation is thus not undertaken exclusively on the basis of local image features, for example an especially high gradient in the image, but first of all a classification of individual image areas based on complex feature combinations is carried out, and a segmentation takes place subsequently by evaluating which of different classifications is assigned a specific image area.

A computation of a three-dimensional model dataset starting from two-dimensional projection images is essentially possible fully automatically.

Projection images in one embodiment of the method may especially be x-ray recordings that were acquired by a C-arm. For reconstruction of a three-dimensional model dataset at least two projection images are necessary, which advantageously have been recorded over an angular range of at least 30°. In order to minimize disruptions resulting from a movement of the blood vessel system between the image recordings, the projection images may advantageously be recorded during the same heart phase. Preferably EKG data may be recorded in addition to the projection images. A retrospective gating is thus possible, in which the projection images of a specific heart phase, especially the end systole or the end diastole, are selected for further processing. As an alternative, an image recording may be triggered via an EKG. As an alternative, it is also possible to record the projection images in any given heart phases and deduce a movement sharpness and thus a heart phase as a result of edge sharpnesses in the image.

As an alternative, the method may also be used for other medical measuring methods that provide projection images of a blood vessel system. For example, the projection images may be acquired in an emission tomography system with an aperture in front of a detector, so that exclusively almost perpendicular incident radiation is detected by the detector.

The image areas may especially involve individual pixels or groups of neighboring pixels. In particular, the image areas are selected so that the image areas do not overlap. Advantageously, each pixel of the projection images is part of at least one image area. The different image areas may especially be the same size or have the same number of pixels. As an alternative, it is also possible to define image areas as a function of previous computations. For example, by a preceding segmentation as a function of an image contrast, especially complex image areas may be selected for which subsequently classification information will be defined.

The classification function in the method especially embodies a so-called multi-class classifier, since the classification function defines whether a respective image area belongs to one of a number of vessel segments of a blood vessel system defined in accordance with anatomical specification data, especially in accordance with an anatomical atlas, or whether the area does not belong to the blood vessel system. The output value of the classification function is one of a number (e.g., especially more than two) items of classification information (i.e., the classification information may divide the image areas into classes, especially more than two classes).

A multi-class classifier may be formed by a number of binary classifiers, which each check the validity of the statement applies as to whether specific image area belongs to a specific vessel segment of the blood vessel system or not. In particular, each of the binary classifiers may output a probability for a validity of the respective classification information, a significance or similar, with which a multi-class classification may take place as a function of the corresponding information of the number of binary classifiers.

The classification function may define a classification as a function of the plurality of weak criteria that are also called basic classifiers or weak learners. Each of these weak criteria evaluates one or more features which are contained in the feature vector or are derived from said vector as to the extent to which this feature corresponds to the weak criterion. The different weak criteria may be combined in a diversity of ways as part of the classification function. For example, decision trees may be constructed from weak criteria, the evaluations of a number of weak criteria may be statistically linked, specific classification information may already be excluded depending on a subgroup of weak criteria before a final definition of the classification information or such like. Depending on the concrete implementation, very many, for example a few hundred or even a few thousand weak criteria, may be evaluated and a plurality of logical linkages is possible for the evaluation results.

An advantage of a classification by machine learning methods is that weak criteria are also able to be used as part of the allocation of the classification information to the feature vector, in which it is not intuitively recognizable that they form a criterion with which image areas are able to be allocated to defined vessel segments.

A weak criterion may be the criterion of "vesselness", which was introduced by A. F. Frangi (cf. A. F. Frangi et al., "Multiscale vessel enhancement filtering", Medical Image Computing and Computer Assisted Intervention—MICCAI '98, Notes in computer science, Vol. 1496, 1998, Page 130 ff.). A high "vesselness" describes that there is a high probability that a tubular object is presented in analyzed image data. Other weak criteria may evaluate mean values of the image area or other segments of the image data at a predetermined position relating to the image area, gradients of corresponding areas, variances of groups of pixels, intensity distributions, for example a wavelet transformation of the image data, or similar. The features to be evaluated may be rotation-invariant or not. The features may be strongly local, for example describe relative intensities of neighboring pixel groups, or the features may involve global features, for example a statistical evaluation of the intensity distribution in the overall image or the result of a transformation of the projection image.

As part of the classification function, a location of the image area may also be evaluated in relation to known organs or further vessel segments. This is especially advantageously possible when the classification function is multi-stage (e.g., initially, for example, there is a first classification, which is confirmed, discarded or adapted by a further classification).

Since the classification function explicitly outputs an allocation of the feature vector to classification information and thereby to a specific vessel segment, a subsequent segmentation is readily possible in that especially contiguous image areas having the same classification information are grouped and considered as one segment.

Thus, the method makes it possible to carry out a segmentation of the blood vessel system fully automatically. The classification information may additionally be used to improve the registration between the different projection images and/or to define image data of which projection images will be included for calculating the characteristics of a specific vessel segment. In addition, it makes possible the use of prior knowledge from medical atlases in the definition of parameters of vessel segments. For example, it may be taken into account that the diameter of a vessel segment always reduces in diameter in the ostial-to-distal direction.

Advantageously in the method, in addition to the image data of the image area assigned to the feature vector or of the computation data computed as a function of this image data, further information is included in the feature vector that is able to be evaluated by the classification function. Such information relevant for classification may especially relate to the direct environment of the image area or the global environment of the image area in the projection images. It is therefore advantageous if the feature vector is assigned additionally at least parts of the image data of at least one further image area that is not assigned to the feature vector and/or includes further computation data computed as a function of this image data. In particular, the feature vector may include the entire image data of that projection image that includes the image area assigned to the feature vector and/or computation data computed from this image data. In addition or as an alternative, image data of further projection images or computation data computed as a function of said data may be accepted into the feature vector.

The reliability and speed of the assignment of classification information may be further improved if the feature vector additionally includes the blood vessel system or additional information describing its mapping. In particular, the additional information may describe a recording geometry of at least the projection image that includes the image area assigned to the feature vector. Advantageously, recording geometries of all projection images are accepted into the feature vector as additional information, the data of which the feature vector at least partly includes or from the data of which values have been computed which the feature vector includes. The recording geometry of the projection image especially describes the recording angle. Further, additional information for the recording geometry may be the position of the patient in relation to the recording device.

In addition or alternatively, the additional information may include patient information, which describes the age and/or the gender and/or symptoms relating to the blood vessel system and/or a height and/or a weight of the patient. Corresponding patient prior information about a probable embodiment of the blood vessel system is already known may be used as part of the classification function.

The method especially enables the model dataset of a blood vessel system with at least two vessel segments to be computed. The vessel segments are assigned different classification information. In particular, by assigning specific image areas to specific vessel segments, blood vessel systems with one or more branches (e.g., blood vessel systems including bifurcations) may be automatically segmented and modeled.

In the method, a dataset, which describes a three-dimensional course of at least one center line of the vessel segment and a vessel diameter at a number of points of the vessel segment, may be defined as a model dataset. For blood vessel systems having bifurcations, a center line may be computed for each vessel segment and the vessel diameter along the number of center lines may be defined.

In particular, for determining the three-dimensional course of the center line in a number of the projection images at least one projection center line of the respective vessel segment may be determined in each case, in accordance with which the center line is determined from the projection center lines as a function of anatomical landmarks recognized in the projection images. In addition or as an alternative, as part of the determination, a recording geometry of the projection images provided as additional information may be taken into account. Since the different image areas of the projection images are assigned to defined vessel segments in the method, bifurcations may be especially easily recognized. In particular, bifurcations may already be distinguished from crossing vessel segments of the blood vessel system in an individual projection image.

The assignment of classification information also enables additional information of an anatomical atlas to be used. Through this additional information, it is especially possible to define center lines of the vessel segments in the projection images entirely automatically. From the center lines of the individual vessel segments in the individual projection images, a three-dimensional center line may subsequently be defined for the entire blood vessel system.

In particular, branches of the blood vessel system may be used as landmarks. The landmarks of different projection images may be assigned to one another as a function of the classification information of the image areas lying in the area of the landmarks. In particular, through the assignment of the different classification information to the image areas immediately adjoining one another in the different projection images, the bifurcations may be uniquely recognized in each case and the bifurcations recognized in the different projection images may be uniquely assigned to one another. Thus, a plurality of landmarks is advantageously present in each of the projection images, with which an especially simple and reliable registration of the projection images or of the vessel segments mapped in the individual projection images to one another is possible.

The classification function may include at least two classification subfunctions in the method through which, as a function of the feature vector an intermediate result is provided in each case, in accordance with which the classification information is defined from the intermediate results of one or more of the classification subfunctions. The classification subfunctions may especially be trained separately with training datasets in each case. The individual classification subfunctions may additionally output confidence values, which describe probabilities, significances or the like for an intermediate result. If the intermediate result from which the classification information is defined includes corresponding statistical information, then the intermediate result with the highest confidence value may be selected as classification information. As an alternative, a number of intermediate results may also be taken into account, such as being weighted as a function of the corresponding values, in order to define the classification information.

The classification subfunctions may interact in different ways in order to provide the classification information. Thus, features of the feature vector or features derived from these features may be used in order to define which of a number of classification subfunctions will be executed in order to define the classification information. For example, different classification subfunctions may be provided for different recording angles, different symptoms of the patient, the gender of the patient, different height ranges of the patient or similar.

As already explained at the start, a number of binary classifiers may also be employed as classification subfunctions in order to jointly provide a multi-class classifier.

The classification subfunctions may be processed serially. A first classification subfunction may supplement a feature vector with an intermediate result, which will be taken into account within a further classification subfunction. As an alternative or in addition, a second classification subfunction performed may be selected depending on the intermediate result of a first classification subfunction.

It is also possible for a first classification subfunction to already sort out certain groups of feature vectors, which are assigned to specific classification information, wherein the further features vectors of following classification subfunctions are further processed. For example, a first classification subfunction may recognize image areas in which artificial objects such as tubes, scissors, or the like are present and assign the classification information to the corresponding image areas that they do not belong to the blood vessel system. The following classification subfunctions are only provided with feature vectors that are assigned to the image areas that do not map such third objects. Thus, classifiers may also be used as these types of classification subfunctions that exhibit a high fault detection of third objects as vessel segments, since corresponding feature vectors have already been sorted out beforehand.

Classification subfunctions may also be used in parallel in addition or as an alternative, wherein a feature vector is supplied to a number of the classification subfunctions and the respective intermediate results are subsequently combined into a common intermediate results by, for example, the result with the highest probability or significance being selected or by the individual intermediate results being statistically logically linked.

The said linkage options of the classification subfunctions may be combined in a wide diversity of ways. In particular, the classification function or at least one of the classification subfunctions may have the structure of one or more decision trees. The classification function or at least one of the classification subfunctions may, for example, use a random forest algorithm, which has a number of uncorrelated decision trees. As a result of the classification function or classification subfunction in this case, the classification information or the intermediate result is a result by most of the uncorrelated decision trees.

In the method, at least one feature vector of one of the training datasets may include image data of a two-dimensional image, which has been generated from a three-dimensional image dataset or from a two or three-dimensional simulation dataset. In particular, annotated 2D projections may be computed from one or more annotated CT datasets. It is also possible to generate simulated image datasets by the use of an anatomical atlas and the simulation of an imaging.

For the determination of a vessel diameter that is as exact as possible, it is advantageous for the center line of a vessel segment to essentially lie in the image plane of the projection image. In addition, covering of the vessel segments with other vessel segments or other overlaying objects, such as bones or the like, should be avoided. Therefore, it is advantageous for at least one part dataset of the model dataset to be computed exclusively from a subset of the projection images that is selected as a function of the classification information or at least one of the items of classification information that is or are assigned to at least one of the image areas. Thus, specific information of the model dataset, especially the course of a vessel center line and/or of the vessel diameter, may only be computed from those projection images for which, for example, by using prior information of an anatomical atlas, it has been defined that the vessel segment of the relevant part of the vessel segment is not covered and/or that the center line of the vessel statement lies essentially in the image plane. Advantageously, additional information describing the recording geometry of the respective projection image is taken into account for this purpose.

In particular, the model dataset of a blood vessel system may be computed with at least two vessel segments, wherein for calculating the part datasets describing the respective blood vessel segments, different subsets of the projection images are used. The subsets are especially selected as a function of the anatomical specification data.

It is possible that in individual projection images no sufficiently clear and unique definition of classification information is possible, which means that these projection images may disturb the computation of the three-dimensional model dataset. It is therefore possible that a confidence value is additionally defined for each of the image areas that describes a reliability of the assignment of the classification information, after which an overall confidence value for the projection image is defined from the confidence values, after which only image data of projection images for which the overall confidence value exceeds a predetermined threshold is taken into account in the computation of the model dataset. As an alternative or in addition, it is possible to already not take into account projection images or image areas during the computation of the model dataset if the confidence value of an individual image areas lies below a predetermined further threshold.

In the method, the feature vector may additionally include in each case at least image data of a projection image, which does not include the image area assigned to the feature vector. In particular, the feature vector may include image data of projection images of which the recording angle is immediately adjacent to the recording angle of the projection image, which includes the corresponding image area. As an alternative or in addition, the feature vector may include image data of a further projection image, which was recorded at a recording angle essentially perpendicular to the recording angle of the corresponding projection image. By taking account of this image data, a particularly good distinction may be made between a bifurcation of the blood vessel system and an overlapping of a number of vessel segments of the blood vessel system in the projection image.

In addition to the method, the embodiments are provided for a computing device, especially a computing device of a medical examination device embodied for carrying out the method.

In addition, embodiments include a computer software product or logic executable by a processor and stored in a non-transitory computer readable medium, which is embodied, when executed on a computing device, for carrying out the method.

Further advantages and details emerge from the exemplary embodiments given below as well as the associated drawings.

DETAILED DESCRIPTION

Figure 1:
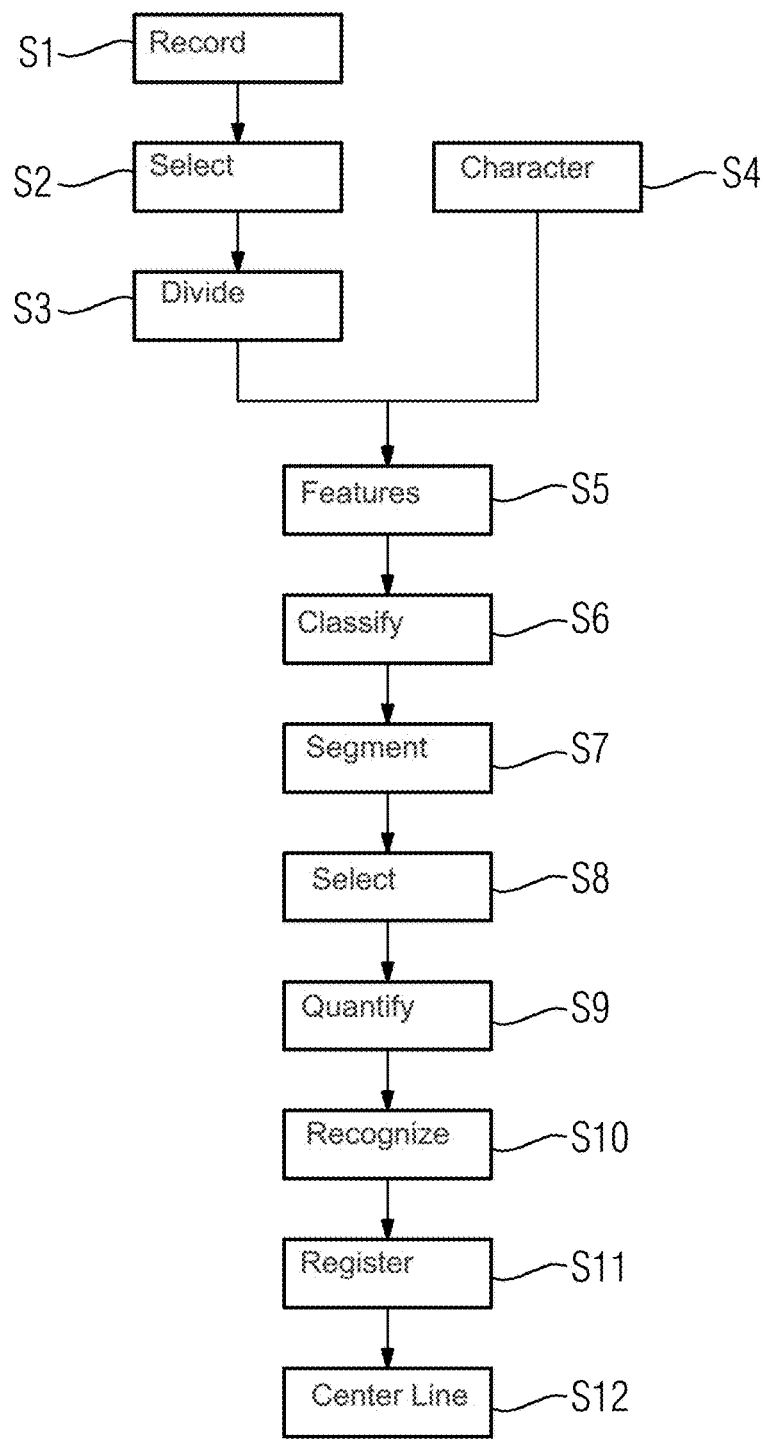
FIG. 1 shows a flow diagram of an exemplary embodiment of a method.

FIG. 1 shows an exemplary embodiment of the method for determining a three-dimensional model dataset of a blood vessel system of a patient including at least one vessel segment. In act S1, as a preparatory act, a number of projection images of a blood vessel system of a patient are recorded from different recording angles with an imaging detection device, namely an x-ray device with a C-arm. In particular, a contrast medium is used during the recording of the blood vessel system. The recording angles of the projection images are selected such that an angular range of at least 30° is covered by the projection images. The recording is triggered by a synchronization of the recordings with an EKG signal such that all recordings occur in the same heart phase, especially during the end systole or the end diastole. A heart phase is selected in which a small movement in the blood vessel system, even in the area adjacent to the heart, is to be expected.

In act S2 the projection images used in the method are selected. In the simplest case, all projection images recorded in act S1 may be used in the method. It is also possible in act S2 however to discard projection images that have low contrast or a high movement unsharpness. The selection of individual projection images for further processing is especially expedient if, in act S1, the recording has not been triggered by an EKG signal. In this case, in act S2 the projection images of a certain heart phase may be selected, for example by evaluation of the detected movement unsharpnesses. Thus, there may be a retrospective gating of the projection images.

The projection images are divided into image areas in act S3. In the simplest case, each pixel of the respective projection image may represent a separate image area. Since the processing of the projection images that follows is relatively computing-intensive however, it is possible for image areas to also be a number of pixels, so that the following classification and segmentation is done with a lower resolution than the pixel resolution of the projection images.

In an alternative embodiment of the method, it would be possible, in act S3, to already provide a pre-segmentation, which divides the individual projection images into areas with essentially the same contrast values. In addition, additional conditions relating to the form of the image areas, especially that these are convex, may be taken into account in the pre-segmentation. In a corresponding pre-segmentation, it is possible to already define areas of a number of contiguous pixels for which it is to be assumed that the pixels are likely to be classified as the same.

In parallel to steps S1 to S3, conclusions are provided in act S4 about the likely characteristics of the blood vessel system and or additional information allowing its imaging in the projection images. These include information about the imaging geometry of the projection images, especially a recording angle, information on the position of the patient in relation to a coordinate system assigned to a detection device and also information about the patients themselves, which allows forecasts to be made about the embodiment of the blood vessel system. The patient information in such cases may especially be information about the gender, the age, the size, the weight, and the symptoms of the patient relevant for the blood vessel system. Thus, for example high blood pressure may lead to deformations of the blood vessel system. A later classification may be made easier on the basis of this additional information.

In act S5, a feature vector is generated for each of the image areas to be classified. The feature vector includes information on the assignment of the image area to one of the projection images, the position of the image area within the projection image, image information of the projection image, image information of projection images with adjacent recording angles, and also relevant additional information, especially the recording geometry of the respective projection image and also patient information.

In act S6, an item of classification information is assigned to each of the feature vectors and thus to each of the image areas. The item describes that the respective image area belongs to a vessel segment of the blood vessel system defined in accordance with an anatomical atlas or that it does not belong to said blood vessel system. For this purpose, the feature vector is processed by a classification function, which maps the feature vector onto corresponding classification information.

The classification function uses machine learning (i.e., the classification function is trained with the aid of annotated training data). The classification function may include a plurality of classification subfunctions, which each provide intermediate results, as a function of which the classification information is determined. The classification function or the classification subfunction each represent so-called weak learners or are made up of such weak learners. A weak learner is understood as a classifier that, because of a relatively simple criterion, for example the variance in contrast in an image segment, assigns to the feature vector a certain class or a probability that the feature vector belongs to this class. Individual weak learners may typically perform a classification as a feature vector only with very low significance. Therefore, as will be explained later with reference to FIG. 3, typically a number of weak learners are combined in order to reach an intermediate result for an item of classification information.

The use of classification functions as part of machine learning is basically known in the prior art and will not be explained in detail. An overview of the learning process for learning the classification function for the method is given in the text below with reference to FIG. 2.

After conclusion of act S6, each of the image areas is assigned classification information. On the basis of the known classification information projection images may be segmented in act S7 in that contiguous groups of pixels in each case, to which the same classification information is assigned, are assigned to a segment of the projection image. Compared to a pure contrast-based segmentation, it is especially achieved that individual segments are always assigned to a defined vessel segment, even if the image areas belonging to the different vessel segments have an almost identical contrast.

A segmentation by machine learning also allows an especially reliable distinction between bifurcations (e.g., branches in the blood vessel system) and mapping of vessel segments crossing in the projection image.

In act S8, there is a second selection of the projection images used subsequently or of the image areas used subsequently. In such cases, use is made of the fact that the classification function, in addition to classification information, also provides a confidence value, which specifies how reliable the assignment of the classification information to the corresponding feature vector or image area is. A confidence value may, for example, be a probability of the correct assignment of the classification information. Projection images for which a mean value of the confidence value across the image areas lies below a predetermined threshold value or which have the individual image areas of which the confidence value lies below a further limit value, are considered as not suitable for model formation and are discarded.

In addition to discarding individual projection images, the choice is additionally made in act S8 of which of the projection images are to be included in each case as part of the modeling of individual vessel segments. Courses of center lines of vessel segments in diameters of vessel segments are to be defined in particular as part of the modeling of the vessel system. In order to make it possible to determine this information as exactly as possible, it is advantageous to select projection images for which the vessel segments to be modeled in each case essentially lie in the image plane of the projection image. In addition, where possible, projection images should be selected in which the respective vessel segment is not covered by a further vessel segments or other objects, for example bones. A corresponding choice of the projection images may be made by using an anatomical atlas. Since it is known which vessel segments is mapped in which image area in each case, optimum recording angles may be defined on the basis of the anatomical atlas, and thus optimal projection images may be selected.

In act S9, the individual vessel segments are quantified in each case in the projection images selected for the respective vessel segment. For each of the vessel segments in the corresponding projection images, a projection center line of the vessel segment and a course of the diameter of the vessel segment along the projection center line is defined. The prior knowledge from an anatomical atlas is used in the quantification. For example, it is known that blood vessels decrease in diameter in their course from an ostial to a distal position. Such use of prior knowledge is possible since each of the vessel segment is uniquely assigned to a vessel segment defined in the anatomical atlas.

In act S10, landmarks, especially bifurcations in the blood vessel system, are recognized in the individual projection images. As an alternative or in addition internal organs, bones or the like may also be recognized as landmarks. A detection of bifurcations is especially simple since bifurcations may be recognized as such points on which image areas are based to which different classification information is assigned, which in each case describes that it belongs to a defined vessel segment. As well as the easy recognition of the landmarks, this also has the advantage that bifurcations are able to be uniquely assigned to one another in the individual projection images since it is known in each case which vessel segments meet at the respective bifurcations.

In act S11, with the aid of the landmarks defined in act S10 and the assignments known in each case as to which of the landmarks in a first projection image corresponds in each case to a landmark in a second of the projection images, a registration of the projection images may be carried out. Depending on this registration, in act S12, a three-dimensional center line is defined for each of the vessel segments from the projection center lines known in each case. In addition, at each point of the three-dimensional center line the vessel diameter from different angles of view is also known so that also the local shape of the vessel may be modeled. A model dataset of the blood vessel system, which includes the vessel segment, is created from the individual vessel segments. The transition of the individual vessel segments to one another is a bifurcation in each case and thus is assigned to a landmark. Just these landmarks will however be used for registration of the individual projection images, so that the bifurcations are already registered with one another.

Figure 2:
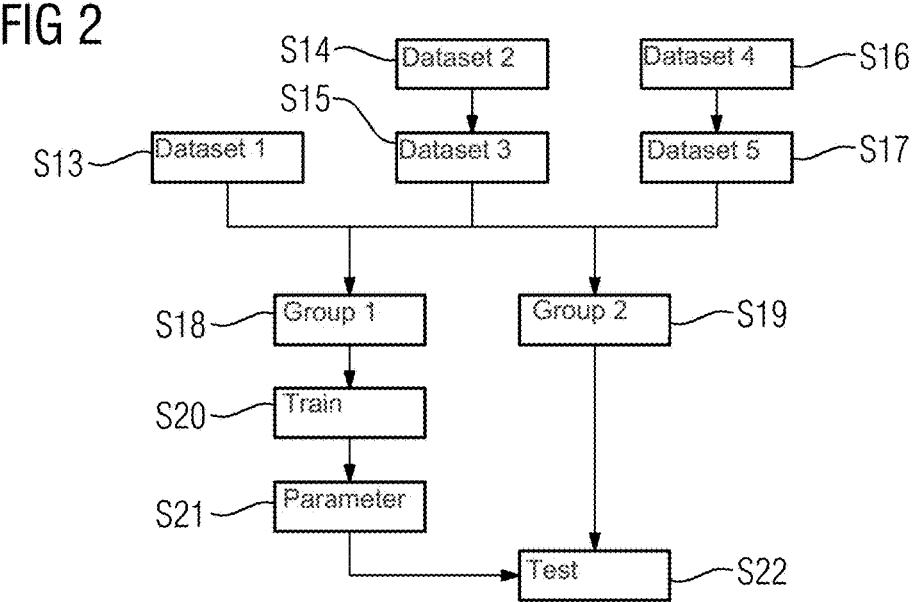
FIG. 2 shows one embodiment of a flow diagram of training a classification function for the method.

FIG. 2 schematically shows a method for provision of training data for training the classification function or classification subfunctions respectively and the training process itself. In steps S13 to S17, annotated training datasets, which include annotated projection recordings of a blood vessel system, are provided, wherein the projection images are divided up into image areas to which in each case an item of classification information is assigned. Several different types of source for training datasets are used.

In act S13, individual projection images, which are recorded with a C-arm or another x-ray device from persons other than the patient and are especially manually annotated, are provided. In act S14, CT data is provided of which the volume dataset is annotated. From this projection images are computed in act S15 of which the respective annotation is derived from the annotation of the volume dataset. In act S16, one or more anatomical atlases are provided for which in act S17 a mapping of the vessel system is simulated. Through the simulated mapping of the vessel system a number of annotated projection images are likewise provided.

The projection images provided are divided into two groups in act S18 and S19. The group formed in act S18 represents the training datasets with which the classification function or the classification subfunctions will be trained. In act S19, a group of test data is provided, via which the success of learning may be tested independently of the training datasets.

In act S20 the classification function or the classification subfunctions are trained. In the simplest case, classification subfunctions each forming a weak learner are trained separately. This will be explained by a simple example. The classification subfunction is to evaluate a "vesselness", meaning the probability that a tubular structure will be mapped. The classification subfunction is to serve as a binary classifier, which outputs whether the respective image area is part of a blood vessel system. In order to determine the "vesselness", a function of the second derivations of the image data of the respective projection image is computed at a position of the respective image area. In such cases, it is assumed that the value of the function correlates with whether an image area is assigned to the blood vessel system or not. Since classification information is known for each of the feature vectors, the respective classification information may be assigned to the function value determined in act S20 (e.g., the "vesselness"). With large amounts of training data, it is possible for different classification information to be assigned to a specific value of the "vesselness". Accordingly the relationship between "vesselness" and classification information may be statistically evaluated in order to determine a most probable assignment.

In act S21, the classification function or the respective classification subfunction is parameterized in accordance with this assignment, so that the subfunction obtains an assignment of the classification function in relation to the training datasets that corresponds as well as possible to the assignment in the annotated training datasets.

Naturally more complex classification functions or classification subfunctions may be trained in steps S20 and S21. A plurality of classification functions and options for training classification functions are known in the prior art. An especially simple example has been selected for the explanation given above but more complex training processes are possible however, in which, for example, a number of classification subfunctions are parameterized or generated in parallel.

In act S22, the classification function or classification subfunction parameterized accordingly in act S21 is tested with the aid of test datasets provided in act S19. In such cases, classification information determined in each case by the classification function or classification subfunction from the test data is compared with the corresponding annotations of the test data in order to obtain information about the reliability of the classification. With the test act S22, information is obtained independently of the actual training process as to whether a corresponding classification is significant, meaning whether its application is expedient or whether another classifier should be used. In addition, a probability of a positive or negative error recognition may be determined, and the trained classification function or classification subfunction may be used in accordance with these values.

Figure 3:
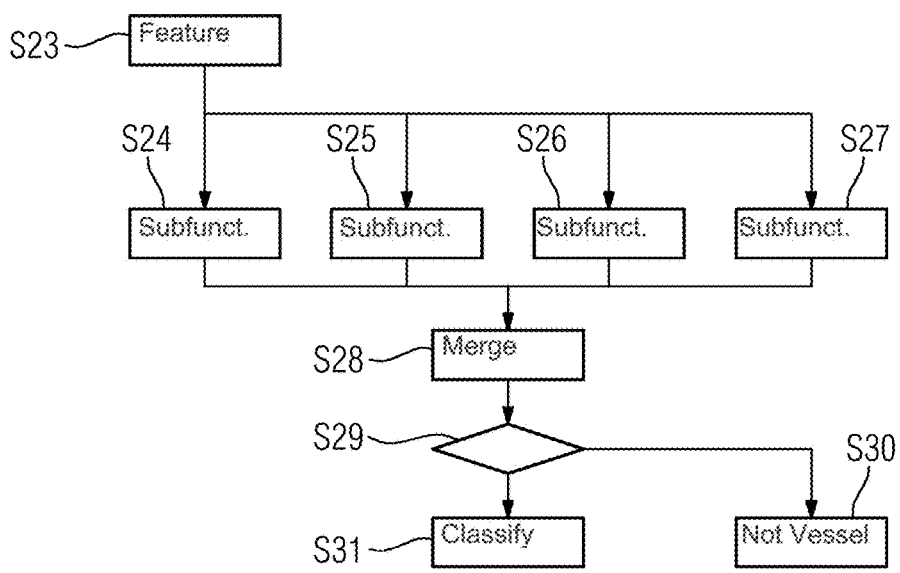
FIG. 3 shows an example for the structure of a classification function in the method.

FIG. 3 shows a possible combination of a plurality of classification subfunctions into one classification function. In act S23, as already explained with reference to FIG. 1, a feature vector is provided to which classification information is to be assigned. For this feature vector, in steps S24 to S27, different classification subfunctions are carried out which, as an intermediate result in each case, output at least one item of classification information for the feature vector and an assigned probability. The intermediate results of the classification subfunctions carried out in steps S24 to S27 are merged in act S28 into a common intermediate result in which the classification information determined by the classification subfunction jointly as most probable classification information is made available.

The merging of results in act S28 could occur in an alternate form of embodiment of the classification function in a different way. For example, the classification information could be output as the intermediate result which has been output by most of the classification subfunctions as classification information. The classification subfunctions of steps S24 to S27 may also be of any given complexity (e.g., include decision trees or similar).

In act S29, it is checked whether act S28 provides as classification information that the image area described by the feature vector belongs to the blood vessel system. If this is not the case, in act S30, as a result of the classification function, the classification information is output that the image area described by the feature vector does not belong to the blood vessel system.

If in act S29, it is established that the feature vector describes that the image area belongs to the blood vessel system, the method is continued with act S31. In act S31, a further classification subfunction is applied to the feature vector. This may, as explained for acts S24 to S28, once again include a number of parallel classification subfunctions, be embodied as a decision tree or similar. The further classification subfunction provides, as a result of act S31, the classification information as a result of the overall classification function.

A serial linkage of classification subfunctions has the advantage that the classification subfunctions of acts S24 to S28 may have other properties than the classification subfunction in act S31. For example it may be very reliably possible through the classification subfunctions of acts S24 to S28 to detect foreign bodies, for example tubes, scissors, or similar in the projection images and to classify image areas which include such objects as not belonging to the blood vessel system. Since such areas were already excluded by acts S24 be S28, a classification subfunction may be used in act S31 which correctly assigns vessel segments with high reliability (e.g., determines correct classification information), however frequently assigns third objects to the blood vessel system. This weak point of the classification subfunction carried out in act S31 has no effect however, since corresponding datasets are already sorted out by acts S24 to S31.

An automatic classification of vessel segments and thus also an automatic segmentation is thus possible by an appropriate choice and linkage of classification subfunctions with high reliability. Advantageously however classification functions or classification subfunctions may be used as an alternative, which automatically perform selection and arrangement of corresponding "weak learners" as part of the learning process. This is achieved for example by so-called random forest algorithms.

A processor, using instructions stored in a non-transitory computer readable medium, performs the method. An x-ray or CT system acquires the data from which features are extracted. A database, such as a patient database, may include data for other features.

Although the invention has been illustrated and described in greater detail by the preferred exemplary embodiment, the invention is not restricted by the disclosed examples and other variations may be derived herefrom by the person skilled in the art, without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a three-dimensional model dataset of a blood vessel system of a patient including at least one vessel segment from a number of projection images of the blood vessel system, the projection images recorded from different recording angles, the method comprising:
dividing the projection images up into image areas each containing at least one pixel,
determining a feature vector comprising at least image data of at least the image area and/or computation data computed as a function of the image data, for each of the image areas,
defining classification information that describes how the respective image area belongs to a vessel segment of the blood vessel system defined in accordance with anatomical specification data or describes how the respective image area does not belong to the blood vessel system, for each of the image areas, the defining being by applying a classification function to the feature vector assigned to the image area, wherein the classification function has been trained by training data records annotated with classification information obtained from at least one person other than the patient,
segmenting the blood vessel system in the projection images by grouping image areas with the same classification information, and
calculating the three-dimensional model dataset as a function of the segmented projection images and the classification information.

2. The method as claimed in claim 1, wherein the feature vector additionally at least includes parts of the image data of at least one other of the image areas that is not assigned to the feature vector, includes further computation data at least computed as a function of said image data, or both.

3. The method as claimed in claim 1, wherein the feature vector additionally includes the blood vessel system or additional information describing mapping of the blood vessel system.

4. The method as claimed in claim 3, wherein the additional information describes the recording angle of at least the projection image that includes the image area assigned to the feature vector.

5. The method as claimed in claim 3, wherein the additional information includes at least one item of patient information that describes an age, a gender, symptoms relating to the blood vessel system, a height, and/or a weight of the patient.

6. The method as claimed in claim 1, wherein the model dataset of the blood vessel system is computed with at least two vessel segments, whereby the vessel segments are assigned different classification information.

7. The method as claimed in claim 1, wherein the model dataset describes a three-dimensional course of at least one center line of the vessel segment and a vessel diameter at a number of points of the vessel segment.

8. The method as claimed in claim 7, wherein, to establish the three-dimensional course of the center line in a number of the projection images, at least one projection center line of the respective vessel segment is determined, after which the center line is determined from the projection center lines as a function of anatomical landmarks recognized in the projection images.

9. The method as claimed in 8, wherein branches of the blood vessel system are used as anatomical landmarks.

10. The method as claimed in claim 8, wherein an assignment of the landmarks of different projection images to one another is a function of the classification information of the image areas lying in a region of the landmarks.

11. The method as claimed in claim 1, wherein the classification function includes at least two classification subfunctions through which, depending on the feature vector, at least one intermediate result is provided, after which the classification information is determined from the intermediate results of one or more of the classification subfunctions.

12. The method as claimed in claim 11, wherein the classification function or at least one of the classification subfunctions has the structure of one or more decision trees.

13. The method as claimed in claim 11, wherein the classification function or at least one of the classification subfunctions implements a random forest algorithm.

14. The method as claimed in claim 1, wherein at least one training feature vector of one of the training datasets includes image data of a two-dimensional mapping that was generated from a three-dimensional image dataset or from a two or three-dimensional simulation dataset.

15. The method as claimed in claim 1, wherein at least one part dataset of the model dataset is computed exclusively from a subset of the projection images that is selected as a function of the classification information of at least one of the classification information which is or are assigned to at least one of the image areas.

16. The method as claimed in claim 15, wherein the model dataset of the blood vessel system is computed with at least two vessel segments, wherein different subsets of the projection images are used to calculate the part datasets describing the respective blood vessel segments.

17. The method as claimed in claim 1, wherein a confidence value is additionally defined for each of the imaging areas, the confidence value describing a reliability of assignment of the classification information, after which an overall confidence value for the projection image is defined from the confidence values, after which only image data of projection images is taken into consideration in the computation of the model dataset for which the overall confidence value exceeds a predefined threshold.

18. The method as claimed in claim 1, wherein the feature vector comprises image data from multiple of the projection images based on the recording angles of the projection images.

19. The method as claimed in claim 1, wherein defining classification information comprises defining in accordance with an anatomical atlas.

20. A system for determining a three-dimensional model dataset of a blood vessel system of a patient including at least one vessel segment from a number of projection images of the blood vessel system, the system comprising:
an x-ray device configured to acquire the projection images recorded from different recording angles;
a processor configured to:
divide the projection images up into image areas each containing at least one pixel,
determine a feature vector comprising at least image data of at least the image area and/or computation data computed as a function of the image data, for each of the image areas,
define classification information that describes how the respective image area belongs to a vessel segment of the blood vessel system defined in accordance with anatomical specification data or describes how the respective image area does not belong to the blood vessel system, for each of the image areas, the defining being by applying a classification function to the feature vector assigned to the image area, wherein the classification function has been trained by training data records annotated with classification information obtained from at least one person other than the patient,
segment the blood vessel system in the projection images by grouping image areas with the same classification information, and
calculate the three-dimensional model dataset as a function of the segmented projection images and the classification information.

21. A non-transitory computer readable medium having logic executable by a processor to determine a three-dimensional model dataset of a blood vessel system of a patient including at least one vessel segment from a number of projection images of the blood vessel system, the projection images recorded from different recording angles, the logic comprising instructions for:
dividing the projection images up into image areas each containing at least one pixel,
determining a feature vector comprising at least image data of at least the image area and/or computation data computed as a function of the image data, for each of the image areas,
defining classification information that describes how the respective image area belongs to a vessel segment of the blood vessel system defined in accordance with anatomical specification data or describes how the respective image area does not belong to the blood vessel system, for each of the image areas, the defining being by applying a classification function to the feature vector assigned to the image area, wherein the classification function has been trained by training data records annotated with classification information obtained from at least one person other than the patient,
segmenting the blood vessel system in the projection images by grouping image areas with the same classification information, and
calculating the three-dimensional model dataset as a function of the segmented projection images and the classification information.

* * * * *